United States Patent [19]

Satoh et al.

[11] Patent Number: 4,732,916
[45] Date of Patent: Mar. 22, 1988

[54] NOVEL GUANIDINOMETHYLBENZOIC ACID DERIVATIVES

[75] Inventors: Toshio Satoh, 57-3, Nagao, Jyoroku-cho, Tokushima-shi, Tokushima-ken; Hitoshi Matsumoto; Hisao Kakegawa, both of Tokushima, all of Japan

[73] Assignees: Kabushiki Kaisha Med-Creat, Tokyo; Toshio Satoh, Tokushima, both of Japan

[21] Appl. No.: 886,158

[22] Filed: Jul. 16, 1986

[30] Foreign Application Priority Data

Jul. 30, 1985 [JP] Japan ................. 60-166903

[51] Int. Cl.$^4$ ................. C07C 129/08; C07C 103/28; A61K 31/65
[52] U.S. Cl. ................. 514/620; 564/164
[58] Field of Search ................. 564/164; 514/620

[56] References Cited

FOREIGN PATENT DOCUMENTS 197256 12/1982 Japan ................. 564/191

OTHER PUBLICATIONS

Markwardt et al., *Pharmazie*, 28(5), pp. 326–330, 1973.
Wagner et al., *Pharmazie*, 30(2), pp. 74–76, 1975.

*Primary Examiner*—Floyd D. Higel
*Assistant Examiner*—Carolyn S. Greason
*Attorney, Agent, or Firm*—Robbins & Laramie

[57] ABSTRACT

A guanidinomethylbenzoic acid derivative represented by the formula

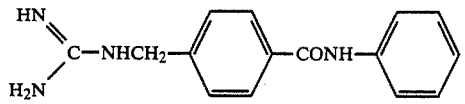

or a salt thereof. An antiulcer agent comprising the compounds of the afore-said formula as an effective ingredient is also disclosed.

2 Claims, No Drawings

NOVEL GUANIDINOMETHYLBENZOIC ACID DERIVATIVES

BACKGROUND OF THE INVENTION

1. Field of the Invention

This invention relates to guanidinomethylbenzoic acid derivatives represented by the formula (I)

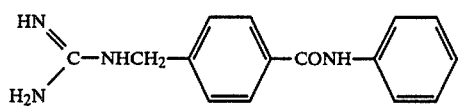

or their salts, and also to antiulcer agents comprising the compounds of the formula (I) as an effective ingredient.

2. Prior Art

A number of compounds have heretofore been proposed for use in the treatment and prevention of gastroenteric ulcers. As disclosed for instance in Japanese Patent Publication (Kokai) No. 57-197256, N-(phenyl)-trans-4-guanidinomethylcyclohexanecarboxamide hydrochloride (hereinafter referred to as a "control compound") posseses the ability to suppress those ulcers, such control compound being represented by the formula below.

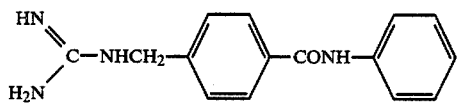

... control compound

The control compound however is not satisfactory in respect of its insufficient antiulcer activity as well as its relatively high toxicity.

Upon synthesis and examination of various compounds as to their antiulcer effects, the present inventors have now found that guanidinomethylbenzoic acid derivatives of the formula (I) or their salts have unexpectedly enhanced antiulcer effectiveness and extremely reduced toxicity, as will appear clear from the animal test results later described.

SUMMARY OF THE INVENTION

It is accordingly an objct of the present invention to provide guanidinomethylbenzoic acid derivatives represented by the formula (I)

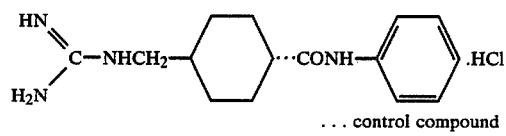

and salts thereof and also acid addition salts thereof. Salts of the compounds of the formula (I) include for example those of inorganic acids such as hydrochloric acid, hydrobromic acid, sulfuric acid, nitric acid, phosphoric acid and the like, and those of organic acids such as acetic acid, propionic acid, citric acid, lactic acid, tartaric acid, p-toluenesulfonic acid and the like. Particularly preferred among those salts are pharmaceutically acceptable acid addition salts.

DETAILED DESCRIPTION

A guanidinomethylbenzoic acid derivative of the formula (I) or its salt according to the invention may be produced for instance by reacting 4-guanidinomethylbenzoic acid (II) and aniline (III) in the presence of dicyclohexylcarbodiimide (hereinafter referred to as "DCC"), and if necessary by converting the resulting free product into the form of a salt.

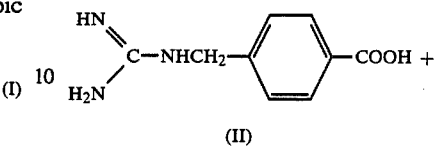

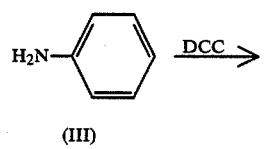

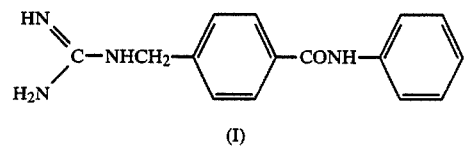

To be more specific, the desired compound (I) may be derived from the dehydrating condensation of the compound (II) with the compound (III) in a solvent in the presence of DCC. The amount of the compound (III) to be used per 1.0 mol of compound (II) is in the range of 1.0 to 1.5 mol. The amount of DCC to be used is in the range of 1.0 to 1.5 mol. Suitable solvents are anhydrous by nature and include acetone, tetrahydrofuran, dioxane, pyridine and the like. The condensation reaction can be fully completed with stirring at room temperature for 10 to 80 hours or with refluxing at the boiling point of the solvent for 1 to 5 hours. Upon completion of the reaction, the reaction mixture is filtrated to remove insoluble matter. The filtrate is concentrated dry, followed by purification of the residue to obtain the compound (I).

The desired compound in the form of an acid addition salt may be directly obtained by reacting an acid addition salt of either one of the compounds (II) and (III) with the other under nonbasic conditions. Bases of both of the compounds (II) and (III) are reacted to free the compound (I) as a base which may be converted in conventional manner to an acid addition salt. Such an acid addition salt of the compound (I) may also be converted to other selected acid addition salts by the use of a salt interchange technique known per se. The compounds (I) or their salts are applicable to the treatment of human beings and warm-blooded animals by oral or nonoral routes (for example, intramuscular injection, subcutaneous injection and local administration).

The compounds contemplated by the invention can be prepared as an antiulcer agent into various forms suitable for oral or nonoral administration in which instance they may be combined with pharmaceutically acceptable, nontoxic carriers in common use. These forms of preparations depend upon the manner in which they are used and include solid forms (for example, tablets, capsules, granules, powders, fine powders, sugar coated pills and troches), semi-solid forms (for example, ointments, creams and suppositories) and liquid forms (for example, injections, emulsions, suspensions, lotions, tinctures, sprays and syrups). Suitable pharmaceutically acceptable, nontoxic carriers include for example starch, gelatin, grape sugar, lactose, fruit sugar, maltose, magnesium carbonate, talc, magnesium stearate, methyl cellulose, carboxylmethyl cellulose (CMC) and its salts, gum arabic, polyalkylene glycols, distilled water for injection use, p-hydroxybenzoic acid alkyl esters, syrups, ethanol, propylene glycol, glycerin, petrolatum, carbowax and the like.

The aforesaid preparations may contain other theraputically useful agents, dispersants, antioxidants, preservatives, stabilizers, perfumes, binders, lubricants, osmotic pressure regulating salts, buffers and the like.

The amounts of the compounds of the invention to be used vary with the forms of preparations, but are preferably in the range of 5 to 100 wt. % in the case of solid and semi-solid preparations and in the range of 0.1 to 10 wt. % in the case of liquid preparations, respectively.

The doses of the compounds of the invention vary widely depending upon the conditions of patients, the kinds of warm-blooded animals to be treated, the symptoms and the diagnoses by the doctors. The compounds may be applied usually in a daily dose of 0.01 to 30 mg/kg of weight, preferably 0.1 to 20 mg/kg of weight. Even those exceeding the above specified doses are suitably applicable according to the symptoms and diagnoses. Dosage may be made at a time or separately a day.

Guanidinomethylbenzoic acid derivatives of the formula (I) or their salts according to the invention are capable of exhibiting excellent antiulcer characteristics as evidenced by the following animal tests.

The tests were conducted with use of the compounds given below.

Test Compounds

A: N-phenyl-4-guanidinomethylbenzamide (compound of Example 1)
B: N-(phenyl)-trans-4-guanidinomethylcyclohexanecarboxamide hydrochloride (control compound)

Test Method 1 (Effect on Stress Induced Ulcer)

1. Test Procedures

The method of Takagi et al (Jap. J. Pharmacol., 18, 9 (1968)) was followed.

SD male rats each weighing from 180 to 200 g (8 weeks of age and 6 to 8 rats in one group) were fasted for 24 hours, followed by oral administration of the above test compounds which had been suspended in 1% CMC aqueous solution. 15 minutes later, the animals were put into a stress cage which was then immersed in a water tank at 24° C. at the depth of the xiphisterna of the animals. After being immersed for 18 hours, the animals were killed under etherization to excise the stomachs. Each of the stomachs was injected with 12 ml of 1% formalin aqueous solution and then immersed in 1% formalin aqueous solution for 15 minutes. The stomach was incised along its upper curvature and measured by an anatomic microscopy for the major axis (mm) of each ulcer that had developed on the gastric mucous membrane. The total major axis (mm) was taken as the ulcer factor. The ulcer inhibition rate was obtained from the following equation. The ED$_{50}$ values were obtained from the doses-ulcer inhibition rates curve.

$$\text{ulcer inhibition rate (\%)} = \left(1 - \frac{m}{l}\right) \times 100$$

where l is the ulcer factor of a group without the test compounds administered, and m is the ulcer factor of a group having such compounds administered.

2. Test Results

The results are shown in Tabel 1.

Test Method 2 (Effect on Ethanol Induced Ulcer)

1. Test Procedures

The method of Robert (Gastroenterology, 77, 433 (1979)) was followed.

SD male rats each weighing from 180 to 200 g (8 weeks of age and 6 to 8 rats in one group) were fasted for 24 hours, followed by oral administration of the test compounds which had been suspended in 1% CMC aqueous solution. After lapse of 30 minutes, 1 ml of ethanol (99.5%) was orally administered. One hour later, the animals were killed under etherization to remove the stomachs. Each of the stomachs was injected with 12 ml of 1% formalin aqueous solution and then immersed in 1% formalin aqueous solution for 15 minutes. The ulcer factor and ulcer inhibition rate were determined in a manner similar to Test Method 1. The ED$_{50}$ values were obtained from the doses-ulcer inhibition rates curve.

2. Test Results

The results are shown also in Table 1.

Test Method 3 (Effect on Indomethacin Induced Ulcer)

1. Test Procedures

The method of Okabe et al (Jap. J. Pharmacol., 29, 670 (1979)) was followed.

SD male rats each weighing from 180 to 200 g (8 weeks of age and 6 to 8 in one group) were fasted for 24 hours, followed by oral administration of the test compounds which had been suspended in 1% CMC aqueous solution, and 15 minutes afterwards, by subcutaneous administration of indomethacin (30 mg/kg of weight) which had been dissolved in 3% sodium bicarbonate aqueous solution. After lapse of 5 hours, the animals were killed under etherization to take out the stomachs. Each of the stomachs was injected with 12 ml of 1% formalin aqueous solution containing 0.1% pontamine sky blue and then immersed in 1% formalin aqueous solution for 15 minutes. The ulcer factor and ulcer inhibition rate were determined in a manner similar to Test Method 1. The ED$_{50}$ values were obtained from the dosesulcer inhibition rates curve.

2. Test Results

The results are shown also in Table 1.

Test Method 4 (Acute Toxicity-Minimum Lethal Dose (MLD))

1. Test Procedures ddY Male mice each weighing from 20 to 22 g (4 weeks of age and 5 mice in one group) were fasted overnight, followed by oral administration of the test compounds which had been suspended in 1% CMC aqueous solution. Observation was made as to the death of the animals over 7 days to thereby determine the minimum lethal doses (MLD).

2. Test Results

The results are shown also in Table 1.

TABLE 1

| Test compound | ED$_{50}$, mg/kg | | | MLD, mg/kg |
| --- | --- | --- | --- | --- |
| | Effect on stress induced ulcer | Effect on ethanol induced ulcer | Effect on indomethacin induced ulcer | Acute toxicity test |
| A | 34 | 35 | 58 | >3000 |
| B | 143 | 220 | 73 | <1000 |

As is clearly evident from the results given in Table 1, Invention Compound A is remarkably effective in suppressing ulcers against stress, ethanol and indomethacin, as contrasted to Control Compound B. Further, the toxicity of Invention Compound A is extremely low as exhibited by its acute toxicity (minimum lethal dose) greater 3,000 mg/kg of weight when orally administered to the mice.

The invention will now be further described by way of the following example.

EXAMPLE

Example 1

(a) Preparation of 4-guanidinomethylbenzoic acid hydrochloride 17.7 Grams of S-methyl isothiourea sulfate was dissolved in 100 ml of 2N sodium hydroxide under cooling, followed by addition of 2N sodium hydroxide up to pH 11 and by subsequent addition of a solution of 10 g p-aminomethylbenzoic acid in 50 ml of boiling water. The resulting solution was allowed to stand overnight at room temperature and thereafter cooled. Crystals thus precipitated were collected by filtration, neutralized by washing with cold water and then dried in vacuo. 99 ml of 1N hydrochloric acid was added to the resulting crystals, and the solution was then heated. Upon removal of insoluble material by filtration, the filtrate was evaporated in vacuo. The residue was recrystallized from water-methanol (1:1) to give 8.4 g of 4-guanidinomethylbenzoic acid hydrochloride as white crystals.

mp: 227°–230° C.

IR(KBr) $\nu$max(cm$^{-1}$): 3400–3000, 1680.

Elemental analysis (as C$_9$H$_{11}$N$_3$O$_2$.HCl): Calculated (%): C, 47.07; H, 5.27; N, 18.30. Found (%): C, 46.98; H, 5.15; N, 18.37.

(b) Preparation of N-phenyl-4-guanidinomethylbenzamide hydrochloride 1.0 Gram of 4-guanidinomethylbenzoic acid obtained in item (a) above and 0.45 g of aniline were dissolved in a solution consisting of 50 ml of pyridine and 20 ml of dimethylformamide, followed by addition of 1.0 g of dicyclohexylcarbodiimide. The resulting mixture was reacted at room temperature for 70 hours. Thereafter, the reaction mixture was added with 50 ml of water and stirred for 30 minutes. Upon removal of insoluble matter by filtration, the filtrate was concentrated to dryness. The residue was washed first with 50 ml of benzene and then with 50 ml of ethyl acetate and recrystallized from water to give 0.5 g of N-phenyl-4-guanidinomethylbenzamide hydrochloride as white crystals.

mp: 178°–180° C.

IR (KBr) $\nu$max (cm$^{-1}$): 3400–3000, 1660, 1600.

MS (e/m): 268 (M$^+$—HCl).

Elemental analysis (as C$_{15}$H$_{16}$N$_4$O.HCl): Calculated (%): C, 59.11; H, 5.62; H, 18.38. Found (%): C, 59.37; H, 5.97; N, 18.84.

What is claimed is:

1. A guanidinomethylbenzoic acid derivative represented by the formula

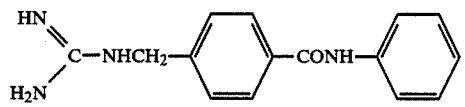

or a salt thereof.

2. An antiulcer agent comprising an effective amount of a guanidinomethylbenzoic acid derivative represented by the formula

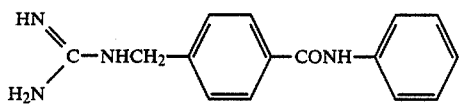

or a salt thereof, and a pharmaceutical carrier.

* * * * *